US006533793B1

(12) United States Patent
Kreiner

(10) Patent No.: US 6,533,793 B1
(45) Date of Patent: Mar. 18, 2003

(54) STEREOTACTIC FRAME

(75) Inventor: Hans Jürg Kreiner, Munich (DE)

(73) Assignee: GKS GmbH, Munich (DE)

( * ) Notice: Subject to any disclaimer, the term of this patent is extended or adjusted under 35 U.S.C. 154(b) by 156 days.

(21) Appl. No.: 09/709,627

(22) Filed: Nov. 13, 2000

(30) Foreign Application Priority Data

Nov. 12, 1999 (DE) .................................. 299 19 920 U

(51) Int. Cl.$^7$ .............................................. A61B 19/00
(52) U.S. Cl. ..................................................... 606/130
(58) Field of Search ........................ 606/130; 600/417, 600/429, 587, 595, 590

(56) References Cited

U.S. PATENT DOCUMENTS 5,752,962 A * 5/1998 D'Urso ........................ 128/857
5,855,582 A * 1/1999 Gildenberg .................. 600/417

* cited by examiner

*Primary Examiner*—John J. Calvert
*Assistant Examiner*—James G Smith
(74) *Attorney, Agent, or Firm*—Crowell & Moring LLP

(57) ABSTRACT

Stereotactic frame having a ring which, for a radiological treatment in the head area, can be supported under pressure on a patient's skill bone by several posts fastened on the ring. A measuring device is provided on at least one post to measure the material deformation on the post resulting from the pressure.

10 Claims, 1 Drawing Sheet

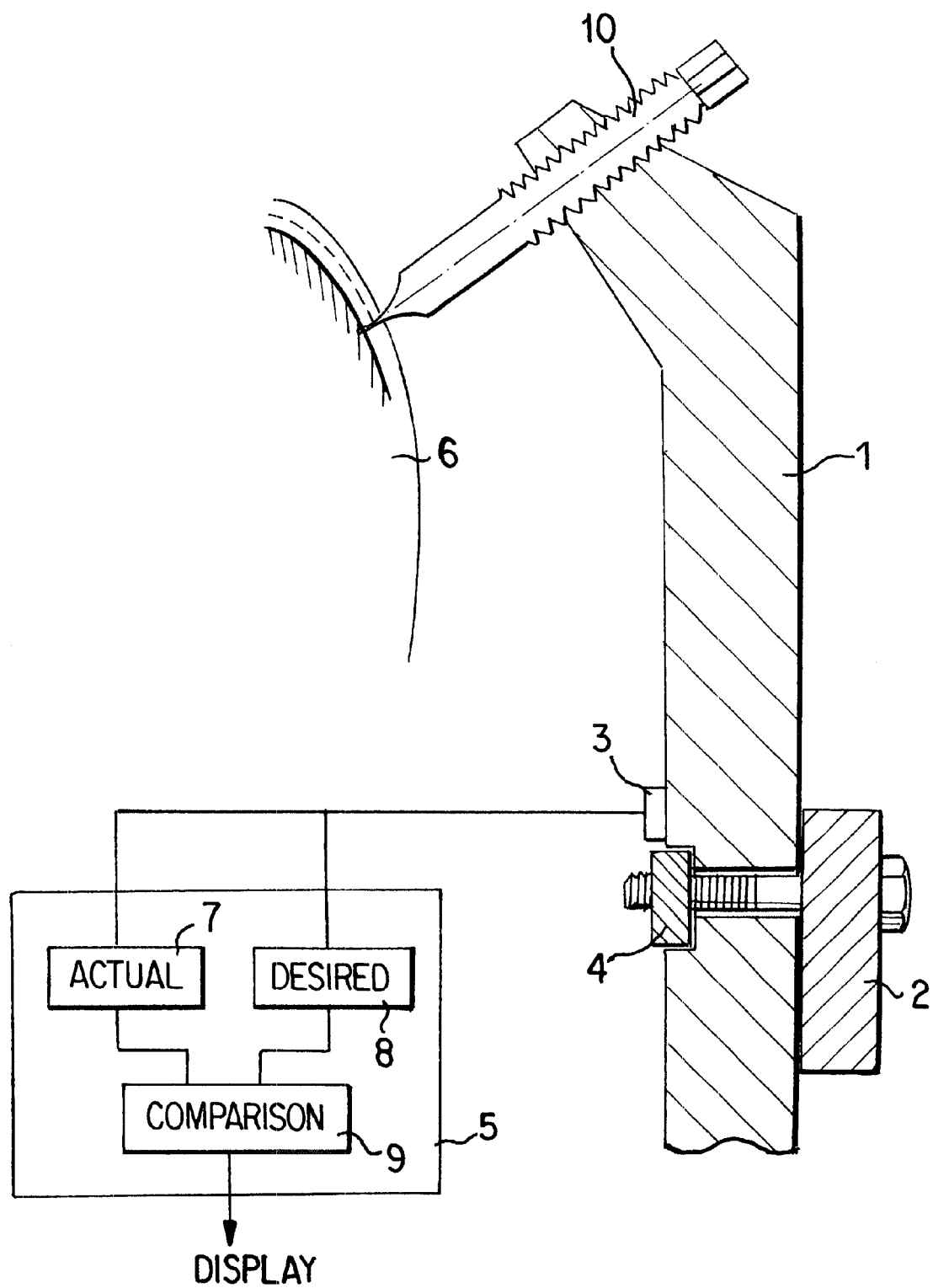

STEREOTACTIC FRAME

BACKGROUND OF THE INVENTION

This application claims the priority of German Application 299 19 920.7 filed Nov. 12, 1999, the disclosure of which is expressly incorporated by reference herein.

The present invention relates to a stereotactic frame having a ring which, for a radiological treatment in the head area, can be supported under pressure on a patient's skull bone by several posts fastened on the ring.

For the radiosurgical treatment, particularly of tumors and other small lesions in the head area, it is known to aim several high-energy radiation sources, particularly gamma radiation sources (Cobalt 60 sources), which are arranged in a helmet, at a radiation center. The tumor to be treated or the lesion to be treated is arranged in this radiation center. This takes place by way of the stereotactic frame, such as a Leksell frame, which is supported on the patient's skull bone and establishes the geometrical reference to the radiation sources.

For the above purpose, the stereotactic frame is clamped to the patient's skull bone by at least one positioning screw, which is provided on one of the posts. During the therapeutic treatment, it is necessary to carry out several adjustments in which the position of the patient's head is changed with respect to the radiation sources. In this case, the danger exists that the ring of the stereotactic frame becomes loose, whereby the geometrical reference between the positions of the radiation sources or of the radiation center at which the radiation sources are aimed, and an accurate position of the patient's head will be lost. This results in the risk that the diseased zone in the head area, for example, in the brain, will no longer be irradiated but adjacent healthy and possibly vital tissue. This risk occurs particularly if the adjustments of the patient's head take place automatically.

SUMMARY OF THE INVENTION

An object of the present invention is, therefore, to provide a stereotactic frame in which a loosening of the stereotactic ring can be determined.

According to the invention, this object has been achieved by providing a measuring device on at least one post. This measuring device measures the material deformation of the post which results from the pressure or tension which supports the stereotactic frame on the skull bone.

In this manner, it is possible to measure the stressing of the stereotactic ring or frame and to determine a change of this stress or a relief and to display a corresponding alarm signal. The present invention is based on the recognition that, during the fastening of the stereotactic frame, relatively high forces act upon certain construction elements of the frame. These forces result in measurable material deformations which can be determined, for example, by wire strain gauges and equally acting measuring elements.

Wire strain gauges are preferably used because they are not susceptible to radioactive radiation and can therefore be used in radiation fields. One measuring device respectively, particularly wire strain gauges, are preferably used on two posts. A loosening of the stereotactic ring causes a clear change of the measuring signal which can be determined and displayed in an analyzing unit connected to the measuring device.

BRIEF DESCRIPTION OF THE DRAWINGS

Other objects, advantages and novel features of the present invention will become apparent from the following detailed description of the invention when considered in conjunction with the accompanying drawings wherein:

The sole FIGURE is a cross-sectional review of relevant portions of the frame according to the present invention positioned in relation to a patient's head.

DETAILED DESCRIPTION OF THE DRAWINGS

The sole FIGURE shows only those components which are essential for understanding the present invention. A closed ring 2, which is illustrated in a cross-sectional view in the FIGURE, of a stereotactic frame is clamped by posts 1 (for example, four posts) to the skull bone of a patient's head 6. A positioning screw 10 is provided on at least one of the posts 1. This support of the stereotactic frame takes place in a known manner. The ring 2 is fastened by a screwed connection in a fastening point 4 at the respective post 1.

In the illustrated embodiment, a measuring device 3 in the form of a wire strain gauge is arranged in direct proximity to the fastening point 4. The measuring device 3 detects elastic deformations of the post material which are caused during the clamping of the stereotactic frame on the patient's head 6. The occurring forces which act upon the post 1 are in the order of from 20 to 30 N.

After the stereotactic frame has been positioned on the patient's head 6, the tension acting in the area of the fastening point 4 at the post material is measured by the measuring device 3 (wire strain gauge) and is stored as a desired value in a desired-value memory 8 of an analyzing device 5. During the therapy procedure, and particularly during the adjustment of the patient's head, a constant measurement of the tension occurring in the area of the fastening point 4 takes place, in which case these actual values, which are supplied by the measuring device 3, are detected in an actual-value memory 7 of the analyzing device 5. By a comparison in a comparator 9 of the analyzing device 5, changes of the forces are determined which act in the area of the fastening point 4.

As soon as the measured changes in forces exceed a threshold value, particularly a percentage deviation, a display particularly an alarm display, is triggered by the analyzing device 4. As a result, a precise and constant monitoring of the fit of the stereotactic frame, particularly of a ring 2, on the patient's head 6 is achieved.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Stereotactic frame, comprising a ring and posts operatively associated with the ring which, for a radiological treatment in a patient's head area, are arranged to support the ring under pressure on a skull bone of the patient, wherein at least one measuring device is operatively arranged with respect to at least one of the posts to measure pressure-related material deformation on the at least one post.

2. Stereotactic frame according to claim 1, where the at least one measuring device is a wire strain gauge.

3. Stereotactic frame according to claim 1, wherein the at least one measuring device is operatively connected with an analyzing device which detects electrically or electronically a change of a measuring signal from a desired value.

4. Stereotactic frame according to claim 3, where at least one measuring device is a wire strain gauge.

5. Stereotactic frame according to claim 1, where the at least one measuring devices comprises a measuring device provided on each of at least two of the posts.

6. Stereotactic frame according to claim 5, where the at least one measuring device is a wire strain gauge.

7. Stereotactic frame according to claim 1, where the at least one measuring device is arranged in direct proximity to a fastening point at which the at least one post is operatively fastened on the stereotactic ring.

8. Stereotactic frame according to claim 7, where the at least one measuring device is a wire strain gauge.

9. Stereotactic frame according to claim 8, wherein the at least one measuring device is operatively connected with an analyzing device which detects electrically or electronically a change of a measuring signal from a desired value.

10. Stereotactic frame according to claim 9, where the at least one measuring devices comprises a measuring device provided on each of at least two of the posts.

* * * * *